United States Patent
Burnes et al.

[11] Patent Number: 5,707,707
[45] Date of Patent: Jan. 13, 1998

[54] COMPRESSIVELY RESILIENT LOOP STRUCTURE FOR HOOK AND LOOP FASTENER SYSTEMS

[75] Inventors: Andrew Scott Burnes, Lawrenceville; Ann Louise McCormack, Cumming, both of Ga.

[73] Assignee: Kimberly-Clark Worldwide, Inc., Neenah, Wis.

[21] Appl. No.: 506,499

[22] Filed: Aug. 1, 1995

Related U.S. Application Data

[63] Continuation of Ser. No. 171,940, Dec. 21, 1993, abandoned.

[51] Int. Cl.$^6$ ............................................ B32B 9/00
[52] U.S. Cl. ............................. 428/95; 428/85; 428/92; 428/94; 428/99; 428/100; 428/102; 428/171; 428/296
[58] Field of Search ................................ 428/94, 95, 93, 428/71, 99, 92, 100, 102, 85, 296, 172, 171; 156/72, 500, 66, 178; 24/442, 444, 450, 451

[56] References Cited

U.S. PATENT DOCUMENTS

| | | | |
|---|---|---|---|
| 3,276,944 | 10/1966 | Levy | 161/150 |
| 3,318,632 | 5/1967 | Struble et al. | 297/220 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,534,852 | 10/1970 | Posner | 206/13 |

(List continued on next page.)

FOREIGN PATENT DOCUMENTS

| | | | |
|---|---|---|---|
| 10962/88 | 7/1988 | Australia. | |
| 803714 | 1/1969 | Canada. | |
| 258015 | 3/1988 | European Pat. Off. | |
| 276890 | 8/1988 | European Pat. Off. | |
| 276970 | 8/1988 | European Pat. Off. | |
| 278866 | 8/1988 | European Pat. Off. | |
| 289198 | 11/1988 | European Pat. Off. | |
| 210536 | 2/1990 | European Pat. Off. | |
| 0604731 | 7/1994 | European Pat. Off. | B32B 31/00 |
| 2009251 | 1/1970 | France | D04H 1/00 |
| 63-145462 | 6/1988 | Japan. | |
| 889943 | 11/1988 | South Africa. | |
| 922698 | 4/1963 | United Kingdom. | |
| 2233876 | 1/1991 | United Kingdom. | |
| WO 92/01401 | 2/1992 | WIPO. | |
| 9220251 | 11/1992 | WIPO | A44B 18/00 |

*Primary Examiner*—Patrick Ryan
*Assistant Examiner*—Abraham Bahta
*Attorney, Agent, or Firm*—Patrick C. Wilson

[57] ABSTRACT

The present invention relates to an improved loop portion of a hook and loop fastening system. The loop portion is a two-layer composite including a compressively resilient backing material and a layer of fibrous loop material. The loop material is placed adjacent the bottom surface of the backing material and then a plurality of the loop fibers are needled or stitched through the backing material to form a plurality of loops which project above the top surface of the backing material. Due to the resilient nature of the backing material, when a hook member is brought into engagement with the loop material, the backing material compresses thereby exposing a greater portion of the individual loops for engagement with the hooks. Once the hooks have been engaged, the backing material expands back to make the exposed portion of the loops smaller. As a result, more individual engagements between hook and loop elements occur and there is less play between the hook members and loop elements thereby yielding a more firmly engaged hook and loop system as evidenced by increased peel strengths when compared to conventionally-backed loop structures. To add increased strength to the structure, the layer of loop material may contain an adhesive to bond the fibers and more firmly anchor the loops so as to lessen the chance of their disengagement during separation of the hook members from the loop members. Lastly, the adhesive employed may be a pressure-sensitive adhesive to permit the adherence of the loop structure to another substrate such as a diaper outercover.

7 Claims, 2 Drawing Sheets

U.S. PATENT DOCUMENTS

| | | | |
|---|---|---|---|
| 3,542,615 | 11/1970 | Dobo et al. | 156/181 |
| 3,595,245 | 7/1971 | Buntin et al. | 131/269 |
| 3,692,618 | 9/1972 | Dorschner et al. | 161/72 |
| 3,694,867 | 10/1972 | Stumpf | 24/204 |
| 3,704,192 | 11/1972 | Soehngen et al. | 156/167 |
| 3,849,241 | 11/1974 | Butin et al. | 161/169 |
| 4,056,281 | 11/1977 | Byrnes | 297/220 |
| 4,340,563 | 7/1982 | Appel et al. | 264/518 |
| 4,389,442 | 6/1983 | Pickens, Jr. et al. | 428/92 |
| 4,739,635 | 4/1988 | Conley et al. | 66/190 |
| 4,741,941 | 5/1988 | Englebert et al. | 428/71 |
| 4,761,318 | 8/1988 | Ott et al. | 428/85 |
| 4,770,917 | 9/1988 | Tochacek et al. | 428/95 |
| 4,776,068 | 10/1988 | Smirlock et al. | 24/442 |
| 4,861,399 | 8/1989 | Rajala et al. | 156/66 |
| 4,931,343 | 6/1990 | Becker et al. | 428/95 |
| 5,032,122 | 7/1991 | Noel et al. | 604/391 |
| 5,256,231 | 10/1993 | Gorman et al. | 156/178 |
| 5,326,612 | 7/1994 | Goulait | 428/100 |
| 5,380,313 | 1/1995 | Goulait et al. | 604/391 |
| 5,407,439 | 4/1995 | Goulait | 604/391 |

COMPRESSIVELY RESILIENT LOOP STRUCTURE FOR HOOK AND LOOP FASTENER SYSTEMS

This application is a continuation of application Ser. No. 08/171,940 now abandoned entitled "COMPRESSIVELY RESILIENT LOOP STRUCTURE FOR HOOK AND LOOP FASTENER SYSTEMS" and filed in the U.S. Patent and Trademark Office on Dec. 21, 1993.

FIELD OF THE INVENTION

The present invention relates to what is commonly referred to as hook and loop fastener systems. More specifically, the present invention relates to a loop portion of a hook and loop fastening system which has a compressively resilient backing material for increasing the peel strength between the hook and loop portions.

BACKGROUND OF THE INVENTION

Hook and loop materials have become a widely used material in today's consumer market. Each day another product has its fastener system replaced by some sort of hook and loop mechanical fastener. Initial fastener systems were relatively expensive and therefore used sparingly. Today, however, as the cost of such materials has decreased, the use of these materials has proliferated. In addition, such proliferation has resulted in the design of a wide variety of materials having varying peel and shear strengths as well as durability.

Peel strength is a term used to describe the amount of force needed to pull apart the male and female parts of the fastener system. The hook portion is often referred to as the male portion and the loop portion is referred to as the female portion. One way to measure the peel strength is to pull one member from the other at a 90 degree angle or, in more common vernacular, by pulling straight up on one of the two pieces.

The shear strength is another measure of the strength of a hook and loop fastener system. Shear strength is measured by engaging the male and female portions and exerting a force along the plane defined by the connected surfaces in an effort to separate the two pieces of material.

Many hook and loop materials are used in areas where they are subjected to considerable movement, twisting and turning. One such use is personal care absorbent articles, including baby diapers and incontinence products. Such products are generally single-use items which are discarded after a relatively short period of use—usually in the range of hours. As a result, it is desirable to avoid expensive components in the design of such products. Conversely, these mechanical fasteners must be able to withstand the rigors of their use with failure in the form of separation of the male and female components giving rise to potentially embarrassing situations for the wearer. Thus, there must be a balance between economy and utility.

It is submitted that one reason for premature separation of the two components of a hook and loop system is that the hook portions have too much play within the loop portions. As the two components are contorted, the hooks and loops move about with respect to one another. In so doing, some of the hooks get pushed down and away from the apexes of the loops. Because of the room between the base of the loops and their apexes, some or all of the hooks can become dislodged from the loops thereby causing the holding strength of the fastening system to be reduced or the members to completely disassociate from one another.

Another proposed reason for premature separation is that the number of individual hook and loop engagements is insufficient to provide adequate attachment due to the failure of the loop fibers to maintain a "z" axis orientation (90°) from the surface of the loop material so as to allow the hook elements to engage the loops and promote a greater number of individual hook and loop engagements. Consequently, there is a need to provide a loop portion for a hook and loop fastener system which, by its design will make it more difficult for the hook portions of a fastening system to disassociate from the loop portions.

SUMMARY OF THE INVENTION

The present invention relates to an improved loop structure for hook and loop fastening systems. Such hook and loop systems have a male portion which includes a plurality of semi-rigid hook-shaped projections anchored to a base material. These hook-shaped projections are designed to engage the loops extending from the loop portion of a hook and loop fastening system. The loop structure of the present invention includes a resilient backing material through which the loops are needled, stitched or otherwise projected from the bottom surface through the top surface. The resilient backing material is made from a nonwoven or foam material having a top surface, a bottom surface and an original thickness. The layer of loop material is either formed directly onto or brought into contact with the bottom surface of the backing material. The loop material may be a fibrous nonwoven web such as a spunbond nonwoven web, or a staple fiber carded web. Alternatively, this layer may be actual yarn or tow. In all cases, the loops on the top surface of the backing material are formed by stitching or needling the fibers/yarn/tow, collectively "fibers" of the loop layer through the top surface of the backing material. The size of the loops and the extent to which they extend above the top surface of the backing material can be adjusted by the degree of stitching or needling of the loop fibers through the backing material. Once the loops have been formed, the fibers forming the loops may be anchored in place by bonding the remainder of the loop fibers still positioned on the bottom surface of the backing material to the bottom surface of the backing material. Bonding is possible through the use of heat and/or adhesives or other suitable means.

The resultant material has an original uncompressed thickness and a second compressed thickness which is less than the original thickness. As the male hook portions are brought into engagement with the female loop members, the resilient backing material is depressed from its original thickness to a second and lesser thickness due to the hook portions pushing down on the backing material. As a result, a larger portion of each of the loops is exposed thereby making engagement of the two pieces easier. Once the male and female pieces have been engaged and the engaging pressure released, the resilient backing material will expand back to a third thickness which is equal to all or at least a major portion of its original height. This in turn leaves less of the vertical height of the loops exposed above the surface of the resilient backing material and forces the hooks more toward the apexes of the loops. Consequently, the hooks have less room to play within the loops. Also, because of the relative thickness of the backing material, the resilient backing material forces the loop fibers into an upstanding or "Z"-directional position thereby increasing the probability of engagement by the hook members. The increase in the number of hook and loop engagements and the "locking" of the loop fibers against the hook apexes results in a loop structure with exhibits improved peel strength.

DETAILED DESCRIPTION OF THE INVENTION

The present invention relates to a novel loop portion for a hook and loop mechanical fastening system. For purposes of illustration only, the present invention will be described separately and in conjunction with its use with personal care absorbent articles including diapers, training pants incontinence garment, sanitary napkins, bandages and the like. As such, the invention should not be limited to these specific uses, as it is instead intended that the present invention be used in all applications where hook and loop fasteners can be employed.

Figure 2:
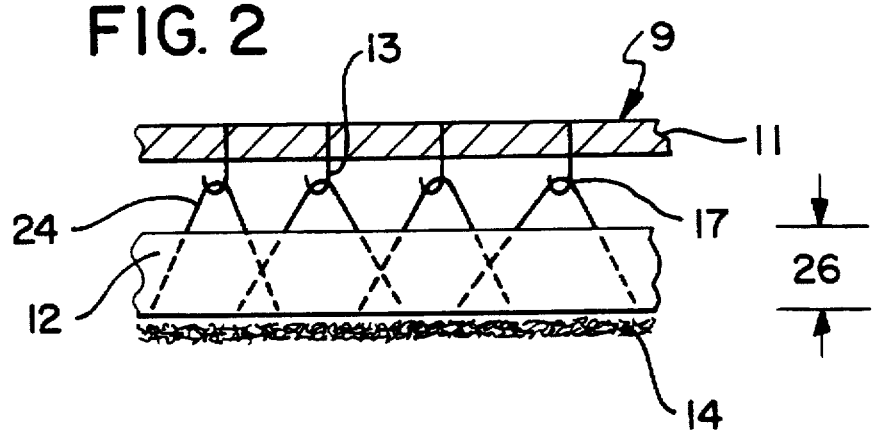
FIG. 2 is a cross-sectional side view of a loop portion according to the present invention fully engaged with a hook portion.
Figure 3:
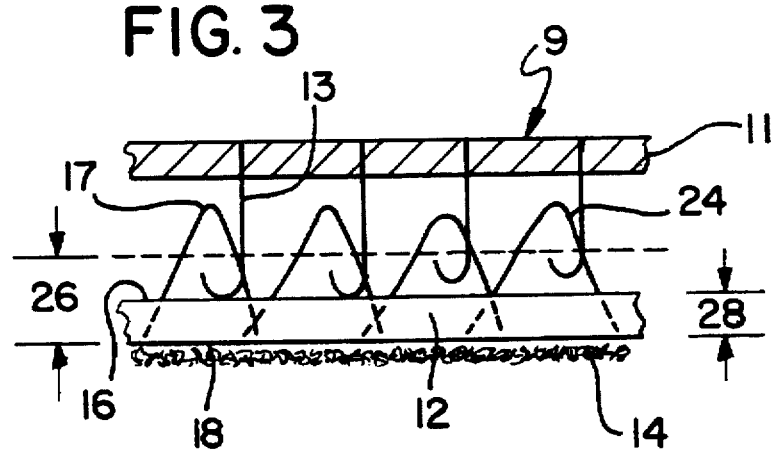
FIG. 3 is a cross-sectional side view of a loop portion according to the present invention during engagement with a hook portion.

In order to achieve constant data regarding the present invention a single type hook material was used to evaluate the material of the present invention. As can be seen in FIGS. 2 and 3, the hook material 9 includes a base layer 11 with a plurality of hook members 13 extending generally perpendicularly therefrom. The hook members 13 have an average overall height measured from the top surface 15 of the base material 11 to the highest point on the hook members 13. The average height of the hook members used in conjunction with the present invention is 0.889 millimeters (mm). The hook material 9 used in conjunction with the present invention is commercially available from Velcro, USA of Manchester, N.H. as Telcar 102 Hook #15. The material comes in 4-inch widths and was used in lengths as outlined in the example.

Figure 1:
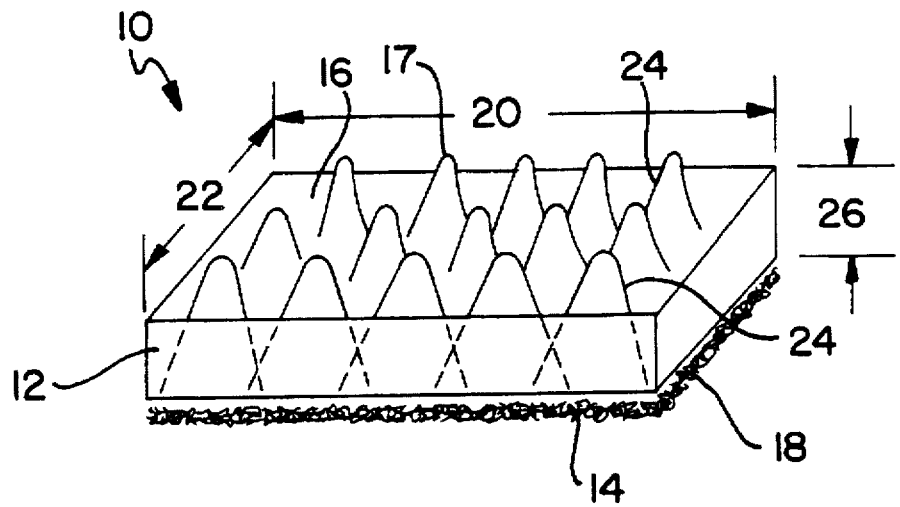
FIG. 1 is a perspective view of a loop portion of a hook and loop fastening system according to the present invention.

Referring to FIG. 1, there is shown a loop portion 10 of a hook and loop fastening system. In its simplest form, the loop structure or portion 10 comprises a resilient backing material 12 and a loop material 14. The resilient backing material 12 can be made form any number of materials so long as it has a compressive resilience as will be explained in greater detail below. Suitable materials would include fibrous nonwoven web materials such as spunbonded, meltblown, air laid, felted and carded webs to name but a few. Foam materials, both open and closed cell, could also be used with the present invention. Furthermore, combinations of the foregoing materials may be used to achieve varying amounts of strength, resiliency and basis weight. As an example, multi-layered composites may be utilized to form the backing material 12. Typically, the backing material 12 will have a basis weight ranging from about 10 to 100 grams per square meter (gsm). However, the actual basis weight can be varied depending upon the particular end use.

In nonwoven embodiments, the resilient backing material 12 may be formed from any polymer, or compound, most typically thermoplastic, which is extrudable into fibers. As a means of illustration only, such polymers may include but are not limited to polyolefins, polyesters and polyamides. These polymers, whether used in generally continuous (spunbond, meltblown and tow webs) or staple form (carded webs) usually have fiber diameters ranging from about 1 to 100 microns. However, these diameters may be varied or different diameters and polymers may be combined to meet a particular need. When staple fibers are used, the fiber lengths will generally range from about 5 to 80 millimeters (mm). Furthermore, the fibers may be self-bonded, thermally bonded or chemically bonded to increase the strength of the material. Care should be taken, though, to maintain the compressive resilience of the backing material 12 when bonding the fibers together.

The resilient backing material 12 may also take the form of a foam, either open or closed cell. Such foams can again, by way of example only, be made from materials including polyurethane and polyethylene. Generally, these foams will have thicknesses ranging from 0.300 to 5 mm.

Referring to FIGS. 1 and 2, the backing material 12 has a top surface 16, a bottom surface 18, a length 20 and a width 22. Extending from the bottom surface 18 through the top surface 16 are a plurality of loops 24 formed from the layer of loop material 14. To form the loops 24 for the present material, a layer 14 of nonwoven material is brought in contact with the bottom surface 18 of the resilient backing material 12. Most typically this nonwoven layer 14 is formed or deposited onto the bottom surface of the resilient backing material 12. The fibers themselves can be continuous fibers such as meltblown fibers and spunbond fibers or noncontinuous fibers such as staple fibers.

Meltblown nonwovens webs are made from meltblown fibers which are formed by extruding a molten thermoplastic material through a plurality of fine, usually circular, dye capillaries as molten threads or filaments into a high-velocity air stream which attenuates the filaments of molten thermoplastic material to reduce their diameters. Thereafter, the meltblown fibers are carried by the high-velocity air stream and are deposited on a collecting surface to form a web of randomly dispersed meltblown fibers. The meltblown process is well known and is described in various patents and publications including NRL Report 4364, "Manufacture of Super-Fine Organic Fibers" by V. A. Wendt, E. L. Boone and C. D. Fluharty; NRL Report 5265, "An Improved Device For The Formation of Super-Fine Thermoplastic Fibers" by K. D. Lawrence, R. T. Lukas, and J. A. Young; and U.S. Pat. No. 3,849,241, issued Nov. 19, 1974, to Butin, et al.

Spunbond webs are made from small diameter fibers and/or filaments which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563, Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

The easiest method of forming a fibrous nonwoven web loop material 14 is to form it directly onto the bottom surface 18 of the resilient backing material 12. The nonwoven layer 14 could also be formed independently and brought together with the backing material 12 just before needling or stitchbonding. The fibers can be made from any of the polymers outlined above for use in the manufacture of the backing material 12. When the layer 14 is made via the spunbonding process the fibers will generally be continuous and have fiber diameters ranging from about 10 to 50 microns. When the layer 14 is made using the meltblowing process, the fibers will have fiber diameters from about 5 to 70 microns. When staple fibers are being used, such as with carded webs, the fibers will generally have a staple length ranging from about 25 to 210 millimeters and fiber diameters ranging from about 10 to 100 microns. Continuous tow fiber which has a continuous fiber length and fiber diameters ranging from about 10 to 100 microns also can be used. Thus, overall, the fibers used to form layer 14 can have lengths from as small as 25 mm and extending all the way to a continuous filament configuration. In addition, the fiber diameters can range from about 5 to about 100 microns. Combinations of fibers based upon polymer selection, fiber size and fiber length also may be used to specifically tailor the layer and loop characteristics. Most typically, the stronger loop materials will be made from higher tenacity, thicker and longer fibers. Typical basis weights will range between about 0.25 and 5 ounces per square yard (osy) (8 and 170 gsm).

Once the loop fibers have been applied to the backing material, they are then needled or stitchbonded through the thickness of the resilient backing material 12 thereby forming a plurality of loops extending from the top surface 16 of the resilient backing material. Such needling may be done by either hydraulic or mechanical means. Typically, flat felt needling loom equipment can be used to form the loops. Such equipment and its use are well known and need not to be disclosed herein in detail. A flat-felt needle loom consists of entry and exit material drive rolls, a reciprocating needle beam, a stripper plate (upper) and a bed plate (lower). The material enters through the entry nip and passes between the stripper plate and a bed plate. The stripper and bed plates are perforated metal surfaces that register according to each needle location on the needle beam. The needle beam reciprocates at 90°, or along the "Z" axis, relative to the plane defined by the plates. On the downward stroke the needle passes through the stripper plate, the loop material 14, the resilient backing material 12 and finally the bed plate. Barbs on the needles engage the loop material fibers and act to entangle them or, as in this application, push the fibers through the resilient backing material 12. As the needle beam retracts the fibers are deposited as loops 24 on the top surface 16 of the backing material 12. Loop characteristics, such as loop height and density, are controlled through various needling parameters. Typically, the depth of penetration of the needle through the backing material and the location of the barbs on the needle dictate the loop height. The frequency of the reciprocation of the needle beam, the speed of the materials through the loom, and the density of the needles on the needle beam determine the loop density (expressed as penetrations per square inch or PPI).

Alternatively, a different type of needling equipment can been used for the formation of the loop material of the present invention. This type of needling is referred to as structured needlepunching which is well known and needs not be described herein in detail. This type of needle loom shares many similarities with flat felt needling; however, instead of the bed plate used in flat felt needling, a brush belt that moves in the machine direction and at the same speed as the material is used. The brush belt is manufactured to rigorous standards with regard to its density and uniformity. This is a particularly desired method of needling loop materials because the brush maintains the vertical or "Z" axis definition of the loops 24 as being distinct from the top surface 16 of the resilient backing material 12. Also, because the brush belt moves with the material, lighter weight and therefore lower cost materials are possible. In the example discussed below, the material of the present invention was produced on a Dilo Di-Lour II structured needlepunching machine from Dilo Inc. of Charlotte, N.C.

As an alternative to forming the loops 24 from a nonwoven material as just described, the loops 24 may also be formed by stitching fibrous materials such as a yarn or monofilaments through the backing material 12 from the bottom surface 18 through to the top surface 16. Such stitching processes are well known and need not be discussed herein.

When stitching the fibers of the loop material through the backing layer, the resultant loops formed on the top surface 16 of the backing layer 12 should project a sufficient distance above the top surface 16 such that there will be sufficient room to securely engage the hook members 13 when the backing layer 12 is in an uncompressed state. Generally in the uncompressed state, the distance between the top surface 16 and the apexes of the loops 24 should be between about 1 and 10 mm. When the engagement of the hooks with the loops takes place, the hooks first encounter the apexes of the loops that have maintained an upstanding orientation due to the supporting effect of the resilient backing material. This "presentation" of the loops to the hook, in itself, increases the number of hook/loop engagements. Further, the hook apexes impinging on the resilient backing compresses the backing material along the "Z" axis of the material, such that more of the loop structure is exposed and available for engagement. The compressional recovery characteristic of the resilient backing material provides for its "rebounding" after engagement which serves to promote the "locking" of fibers that have engaged hooks resulting in elevated shear and peel values.

Once the loops 24 have been formed, they must be secured to the backing material so that detachment of the hooks 13 will not pull the loops 24 out of the backing material 12. To accomplish this, the portion of the fibers/hooks 24 remaining on or adjacent to the bottom surface 18 of the backing material 12 should be attached thereto. Most desirable, the fibers of the loop material 14 are bonded to the bottom surface 18 of the backing material 12 by such means as adhesives, thermal bonding, ultrasonic bonding or a combination of such means. A wide variety of adhesives will work including, but not limited to, solvent-based, water-based, hot-melt and pressure sensitive adhesives. Powdered adhesives can also be applied to the materials and then heated to activate the powder adhesive and perfect bonding. Typically, adhesive add-ons will be in the range of 10 to 40 mg/in$^2$ (15 gsm to 61 gsm).

Figure 4:
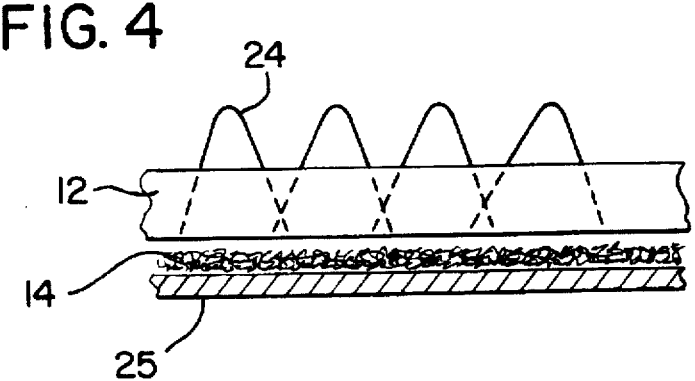
FIG. 4 is a cross-sectional side view of another embodiment of a loop portion according to the present invention.

In certain situations, simply using as adhesive to bond the fibers/loops 24 of the loop material 14 to the backing layer 12 may not provide enough strength. As a result, it is possible to add a support layer 25 to the side of the loop material 14 opposite the backing layer 12 using the same or additional adhesive used to anchor the fibers of the loop material 14 to the backing layer 12. See FIG. 4.

Figure 5:
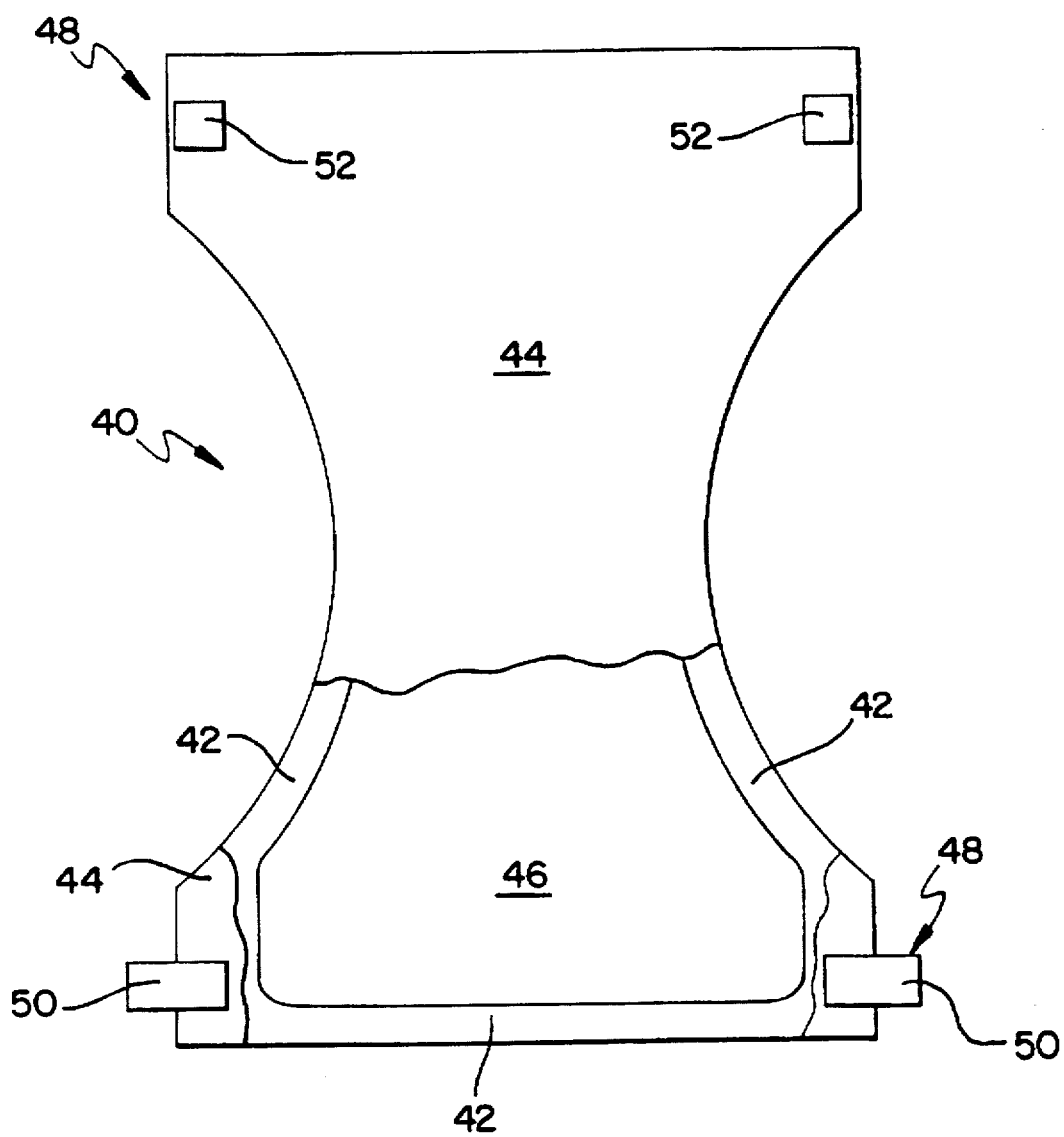
FIG. 5 is a partial cut-away top plan view of a personal care absorbent article, in this case a diaper, employing a hook and loop fastening system according to the present invention.

A particular advantage of pressure sensitive adhesives is the fact that they can also be used to adhere the resultant loop portion 10 to another structure such as the outercover of a diaper. Such is the case in FIG. 5 of the drawings. In FIG. 5 there is show a personal care absorbent article 40, in this case a diaper. The diaper 40 as with most personal care absorbent articles includes a body side liner 42 and a outercover 44. Disposed between the body side liner 42 and the outercover 44 is an absorbent core 46. To secure the diaper about the wearer, the diaper will have some type of fastening means 48 attached thereto such as to the outercover 44. In FIG. 5 the fastening means 48 is a hook and loop fastening system including a hook portion 50 and a loop portion 52 made from the material of the present invention. If the adhesive used to secure the loops 24 to the backing material 12 is a pressure sensitive adhesive, the adhesive can also be used to adhere the loop portion 52 to the outercover 44.

As shown in FIG. 1, the backing material has an original or uncompressed thickness 26 an a compressed thickness 28 as shown in FIG. 2. The uncompressed thickness relates to when the loop material is basically at rest either before a hook material 9 has been engaged with the loops 24 or at some point in time after the hook material 9 has been engaged and the backing material 12 has had time to relax and resume, to the extent possible, its normal state of expansion. The compressed thickness 28 relates to the thickness of the resilient backing material as the hook members 13 are being engaged with the loop members 24 of the system. During this time of compression, the backing material 12 is depressed as the hooks 13 are pressed into the loops 24 thereby reducing the thickness of the backing material 12 and exposing more of the loops 24. During compression, the backing material increases in density and helps the loop fibers maintain a 90° orientation relative to the plane of the backing material 12 for engagement with the hook members 13. Once the backing material 12 relaxes, the backing material 12 expands backs towards its uncompressed thickness 26 so that less of the loops 24 are exposed above the top surface 16 of the backing material 12. As a result, the hooks 13 become better locked into the loops 24 thus making disengagement of the hooks 13 more difficult. This in turn increases the peel and shear strength of the hook and loop material and therefore yields a stronger fastening system.

While the resilient backing material 12 is in its uncompressed state as in FIG. 2, it has an uncompressed thickness and the loops 24 have a first average height which is measured from the top surface 16 of the resilient backing material 12 to the apexes 17 of the loops 24. When the resilient backing material 12 is in a compressed state and thus has a compressed thickness as in FIG. 3, the loops 12 have a second average height which also is measured from the top surface 16 of the resilient backing material 12 to the apexes 17 of the loops 24. The second average height should be greater than the first average height due to the compressed thickness being less than the uncompressed thickness. To calculate the "average height", a measurement of twenty loops is taken, the two highest and two lowest values are disregarded and the sum total of the remaining heights is divided by 16 to yield an average.

The peel strength of the material is a gauge of the functionality of the material. To determine the strength of the loop structure according to the present invention, two tests were run. The first was a static shear test, the second was a T-Peel test. In each of these tests the hook member comprised a continuously injection-molded hook. The hook material had a basis weight of 325 grams per square meter and a thickness of 12 millimeters. Hook density was approximately 1,110,000 hooks per square meter. The standard dimension for the hook samples used in both test methods was 25.4 mm×101.6 mm with the hook direction was oriented such that the hooks "pointed" across the short axis of the sample. This hook material was produced by Velcro, USA of Manchester, N.H. and is available as Telcar 102 Hook #15.

Static Shear Test

The static shear test was used primarily to determine the stability of the hook and loop system after engagement and while under a shear loading. It is a pass/fail test where the fastening elements are engaged and a weight is hung from the loop material for a period of 24 hours. If the fastening system continues to support the weight after the 24-hour interval, the material is said to have passed. The test procedure is as follows:

1. Cut the loop material being tested to 50.8 mm×101.6 mm.
2. Place the loop material, loop side up, on a flat surface and overlay the above-described hook material onto the loop material such that 645.16 mm² (1 square inch) of hook material covers the loop material.
3. Engage the hook and loop portions by rolling the sample with a 4.5 lb hand roller for 5 forward and backward cycles.
4. Secure the hook material vertically such that the loop material hangs free in space.
5. Affix a 500 gram weight to the bottom edge of the loop material and begin timer.
6. If the fastening system continues to support the weight after 24 hours, the test is passed.

90° Peel Strength Test

The 90° peel strength or T-peel test involved attaching a hook portion to a loop portion of a hook and loop fastening system and then separating the two components at a 90° angle. The amount of force needed to separate the two plies was recorded in grams. To perform the test, a tensile tester with a 2000 gram full scale load is needed such as an Instron® Model 6021 tensile tester and a laterally moving jig to keep the point of separation between the hook portion and loop portion vertically centered within the jaws of the tensile tester. The jig includes a 2 inch×6 inch×1/16 inch thick stainless steel panel and the jig is attached to the lower jaw. Down the entire length of the stainless steel panel there is attached a 1½ inch wide double-coated piece of adhesive tape. Next, a 1 inch by 4 inch sample of the loop material is positioned on top of the adhesive tape. To ensure adequate and uniform adhesion between the tape and the loop portion, a 4.5 pound hand roller is rolled down the loop material for two cycles with one cycle equaling a forward and backward stroke of the hand roller. Next, a 1 inch by 4 inch hook portion is positioned over and laid on top of the loop portion. To engage the hook and loop portions, a 4.5 pound hand roller is again rolled over the combined hook and loop portions for five complete cycles. A piece of the short end of the hook material is then peeled away from the loop material and secured within the upper jaw of the tensile tester. The tensile tester is then activated at a crosshead speed of 300 mm per minute and the average load in grams to separate the two materials at a 90° angle is then recorded.

Having thus described the general parameters for the material of the present invention, the processes for making it and the methods for testing it, an illustrative sample was prepared and tested to demonstrate the attributes of the present invention.

EXAMPLE 1

In Example 1, a sample loop portion according to the present invention and a control loop material were prepared and then evaluated. The loop portion of the present invention included a resilient backing material, a loop material and an adhesive. The control sample used the same loop material and adhesive, however, a polyethylene film was substituted for the resilient backing material.

The backing material was a three-dimensional textured meltblown polyethylene nonwoven web with a basis weight of 1.2 osy and an average fiber diameter of 10 microns made in accordance with the teachings of U.S. Pat. No. 4,741,941 to Englebert et al. which is incorporated herein by reference in its entirety. The resiliency and bulk characteristics of the backing material are defined by the compressional loading and recovery data below. As shown by the data below, these resiliency characteristics were responsible for the elevated peel strength of this material relative to the control sample with a non-resilient backing material.

The loop material was needled into the backing material to form the actual loop structure. The loop material comprised a 2.5 osy (85 gsm) carded web with 9 denier polyester staple fibers with a 6 inch cut length. The crimp and fiber finish were standard for a carding fiber. Fiber tenacity was also typical for polyester at 4.0 grams per denier (gpd). The adhesive was a pressure sensitive adhesive.

The process to integrate these components began with the carding of the loop staple fibers into a 2.5 ounce per square yard (osy) (85 gsm) carded web with a fiber MD/CD ratio of 3–6:1. The unbonded carded fiber web loop material was then wound up with the 1.2 osy meltblown backing material. The unbonded carded fiber web loop material and meltblown backing material were then fed into a 600 mm wide pilot scale Di-Lour II machine with the backing material oriented against the brush belt. The needling process was conducted using the following parameters:

Needle type: Foster 35 gauge Star Blade Crown (0.003 inch barb depth)
Needle board density: 150 needles/linear inch
Depth of penetration: 8 mm
Stripper plate height: 8 mm
Penetrations/in$^2$ (PPI): 800
Line speed: 20 feet per minute (FPM)

The needled fiber/meltblown web was then adhesively bonded together. The adhesive was applied to the unbonded carded web fiber on the non-loop side of the meltblown backing material and a sample of the composite was then nipped to an approximately 2 mil thick polyethylene film of a standard diaper in a fashion such as is shown in FIG. 5 using the pressure sensitive adhesive. The process parameters for the adhesive application were as follows:

Adhesive type: Findley 2096
Grams/Min at a 10 inch application width: 175
Nip Gap: 0.00 inches
Slot Gap: 0.005 inches
Slot Shim: 0.010 inches
Line Speed: 50 feet per minute (FPM)
Application Temperature: 330° F.

The adhesive component in this structure served a dual function. First the adhesive acted to stabilize the loop fibers when applied to the non-loop side of the backing material and it also provided a means to adhere the material to a diaper outercover film. The adhesive used in this example was a Findley 2096 pressure-sensitive adhesive from Findley Adhesives, Inc. of Wauatosa, Wis. which was applied using a slot coating applicator head. Adhesive add-on-levels must be sufficient to anchor the loop fibers to the product, in this case a polyethylene diaper outercover film. The adhesive add-on level was 19.2 mg/in$^2$.

A control sample having identical processing parameters and components with the exception of the backing material was also prepared to act as a comparison with the material of the present invention. The backing material of the control was a 0.06 mm thick embossed polyethylene film. The backing material of the control sample did not possess the compressional resiliency characteristics of the backing material of the present invention. While the percentage of bulk recovery was higher after compression, there was insufficient bulk differential between the compressed and uncompressed thicknesses.

Both the material of the present invention and the control were tested using the 90° peel test method described above. A series of five replications were performed for each material. The material of the present invention which utilized the 1.2 osy resilient meltblown backing material had a peel strength of 1020 grams while the polyethylene film backing material control had a peel strength of only 548 grams, thus demonstrating the superior peel strength of the material of the present invention.

In addition to the 90° peel test, both the material of the present invention and the control were tested for static shear. Both materials passed.

An important feature of the present invention is the ability of the resilient backing material 12 to have an original thickness under no load, be able to be compressed to a second and lesser thickness when under load and then, upon release of the compressive load, spring back to an uncompressed third and final thickness which is 60% or more of the original thickness. Using bulk as the measurement of the thickness of the resilient backing material, a compressive resiliency test was performed on both the material of the present invention the control loop structure. For both backing materials, the initial bulk was determined. Next each of the materials were separately placed under a 1.5 pound per square inch compressive load for a period of 60 seconds and then the load was removed. The bulk while under the 1.5 pound per square inch load was measured as well as the bulk after the release of the compressive load. These values are set forth in Table I below. The compression under load data for the control material was taken manually using a Mitutoyo Digimatic Indicator Serial No. 000269 and free weights while the compression under load data for the meltblown resilient backing material was generated on an Instron® Model 6021 tensile tester.

TABLE I

|  | Control PE Film | Meltblown Backing Material |
|---|---|---|
| Original Bulk | 0.06 mm (A) | 1.041 mm (A) |
| Bulk at 1.5 psi | 0.05 mm (B) | 0.279 mm (B) |
| Bulk at 0 psi | 0.06 mm (C) | 0.762 mm (C) |

The initial uncompressed bulk was designated "A" while the compressed bulk was designated "B" and the bulk after one compression cycle was denoted as "C". A relationship between these three values is set forth by the following two equations:

$$A-B>0.3\ A>0.250\ mm\ \text{and}\ C>0.6\ A$$

To be an effective resilient backing material for use with the present invention, the difference between the original bulk and the compressed bulk should be greater than 30% of the original bulk and this value in turn should be greater than 0.250 mm. Once the compression force has been released, the bulk C should be greater than 60% of the original uncompressed bulk or thickness A.

Substituting the values from Table I into the two equations above, it can be seen that the quantity A minus B for the control was equal to 0.01 mm which was less than 0.3 times the original thickness (0.06 mm) and less than the value of 0.250 mm. Thus, the control backing material did not satisfy the first portion of the above-identified relationship, i.e. it would not compress sufficiently. Due to the extreme density of the polyethylene film, the bulk or thickness C of the control backing after the release of the load was equal to the original bulk A and therefore the material satisfied the second half of the relationship.

Performing the same analysis on the meltblown backing material of the present invention, the difference between the original bulk A and the bulk B at 1.5 psi was 0.762 mm which was greater than 0.3 times A (0.312 mm) and greater than 0.250 mm. Thus, the material of the present invention satisfied the first portion of the relationship in that the material could be compressed but not unduly collapsed. The material of the present invention also satisfied the second portion of the relationship in that the bulk C after compression was 0.762 mm which was greater than 0.6 times A (0.625 mm). This then demonstrated that the material of the present invention could be compressed and then, after release of the compressive forces, the material could recover to at least 60% of its previous thickness.

Reviewing the data as a whole, it can be seen that the loop structure of the present invention had excellent peel strength, nearly double that of the control, good static shear properties and a resilient backing material that could be compressed to expose more of the loops and then recover to a sufficient degree to maintain good closure between the hook and loop portions of the fastening system.

Having thus described the invention in detail, it should be apparent that various modifications and changes can be made in the present invention without departing from the spirit and scope of the following claims.

What is claimed is:

1. A loop structure for a hook and loop fastening system comprising:
    a backing material having a length, a width and a thickness and further defining a top surface and a bottom surface, and
    a layer of loop fibers positioned adjacent said bottom surface of said backing material, a plurality of said loop fibers extending through said backing material from said bottom surface through said top surface and forming a plurality of loops which extend from said top surface for engaging a hook member,
    said backing material having an uncompressed thickness wherein said loops have a first average height measured from said top surface of said backing material and a compressed thickness wherein said loops have a second average height measured from said top surface of said backing material, said second average height being greater than said first average height.

2. The loop structure of claim 1 wherein said backing material comprises a foam material.

3. The loop structure of claim 1 wherein said backing material comprises a fibrous nonwoven web.

4. The loop structure of claim 3 wherein said fibrous nonwoven web has a basis weight ranging from about 10 to about 100 grams per square meter.

5. The loop structure of claim 1 wherein said layer of loop fibers is secured to said bottom surface of said backing material.

6. The loop structure of claim 1 wherein said backing material has a thickness difference between said uncompressed thickness and said compressed thickness which is greater than 0.250 millimeters.

7. A personal care absorbent article comprising:
    a body side liner and an outercover with an absorbent core disposed therebetween and a hook and loop fastening system for securing said article about a wearer, said system including a backing material having a length, a width and a thickness and further defining a top surface and a bottom surface, and
    a layer of loop fibers positioned adjacent said bottom surface of said backing material, a plurality of said loop fibers extending through said backing material from said bottom surface through said top surface and forming a plurality of loops which extend from said top surface for engaging a hook member,
    said backing material having an uncompressed thickness wherein said loops have a first average height measured from said top surface of said backing material and a compressed thickness wherein said loops have a second average height measured from said top surface of said backing material, said second average height being greater than said first average height.

* * * * *

UNITED STATES PATENT AND TRADEMARK OFFICE
CERTIFICATE OF CORRECTION

PATENT NO. : 5,707,707
DATED : January 13, 1999
INVENTOR(S) : Burnes et al.

It is certified that error appears in the above-identified patent and that said Letters Patent is hereby corrected as shown below:

Column 2, Line 67, "with" should read -- which --;
Column 3, Line 51, "form" should read -- from --;
Column 5, Line 59 "been" should read -- be --; and
Column 7, Line 15, "an" should read -- and --.

Signed and Sealed this

First Day of June, 1999

*Attest:*

Q. TODD DICKINSON

*Attesting Officer*   *Acting Commissioner of Patents and Trademarks*